United States Patent
Bortfeld et al.

(10) Patent No.: US 6,728,336 B2
(45) Date of Patent: Apr. 27, 2004

(54) ARRANGEMENTS AND METHODS FOR TREATING A SUBJECT

(75) Inventors: Thomas Bortfeld, Cambridge, MA (US); Christian Thieke, Boston, MA (US); Andrzej Niemierko, Wayland, MA (US)

(73) Assignee: General Hospital Corporation, Boston, MA (US)

( * ) Notice: Subject to any disclaimer, the term of this patent is extended or adjusted under 35 U.S.C. 154(b) by 0 days.

(21) Appl. No.: 10/195,910

(22) Filed: Jul. 15, 2002

(65) Prior Publication Data

US 2004/0008822 A1 Jan. 15, 2004

Related U.S. Application Data

(60) Provisional application No. 60/395,496, filed on Jul. 12, 2002.

(51) Int. Cl.[7] .................................................. A61N 5/10

(52) U.S. Cl. ............................... 378/69; 378/64; 378/99
(58) Field of Search ............................. 378/64, 65, 901

(56) References Cited

U.S. PATENT DOCUMENTS 6,459,762 B1 * 10/2002 Wong et al. .................. 378/65
6,546,073 B1 *  4/2003 Lee .............................. 378/65
6,560,311 B1 *  5/2003 Shepard et al. ............... 378/65

* cited by examiner

*Primary Examiner*—David V. Bruce
(74) *Attorney, Agent, or Firm*—Baker Botts LLP

(57) ABSTRACT

An arrangement and method for treating the subject are provided, using which it is determined whether an equivalent uniform dose ("EUD") associated with a particular dose distribution is greater than a first dose tolerance associated with a first structure within a subject. Also, a determination is made as to whether the EUD associated with the particular dose distribution is greater than a second dose tolerance associated with a second structure within the subject.

96 Claims, 8 Drawing Sheets

ARRANGEMENTS AND METHODS FOR TREATING A SUBJECT

RELATED APPLICATION

This application claims priority under 35 U.S.C. §119 to U.S. Provisional Patent application Ser. No. 60/395,496 entitled "ARRANGEMENTS AND METHODS FOR TREATING A PATIENT", filed on Jul. 12, 2002, the entire disclosure of which is incorporated herein by reference.

FIELD OF THE INVENTION

The present invention relates generally to arrangements and methods for treating a subject. In particular, the present invention is directed to arrangements and methods are provides which simulate an application of amount of energy upon a target area, determine whether an equivalent uniform dose ("EUD") associated with a portion of the energy received by a first structure is greater than a dose tolerance of the first structure, and/or determine whether an EUD associated with a portion of the energy received by a second structure is greater than a dose tolerance of the second structure.

FIELD OF THE INVENTION

The present invention relates generally to arrangements and methods for treating a subject. In particular, the present invention is directed to an arrangement and method in which a computer system executes a computer program, and determines whether an equivalent uniform dose associated with a particular dose distribution is greater than a dose tolerance associated with a first structure within the subject and/or a dose tolerance associated with a second structure within the subject.

BACKGROUND OF THE INVENTION

Chemotherapy, surgery, and radiotherapy are three of the most prominent methods of treating cancer and/or tumors in a subject. Radiotherapy is particularly useful when the cancer is restricted to a primary target area (e.g., when there are no metastases), and/or when the target area may not accessed via surgery. Certain conventional radiation therapy treatment plans are iterative forward processes, in which initial parameters (e.g., radiation beam intensity and radiation beam direction) are selected to produce an initial spatial dose distribution (e.g., radiation beam intensity and/or radiation beam direction may determine the spatial dose distribution), and the initial parameters are successively altered until a desired spatial dose distribution is achieved. Other conventional radiation therapy treatment plans are inverse processes which begin with the desired spatial dose distribution, and operate backwards to determine the treatment parameters that will come the closest to achieving the desired spatial dose distribution. The process for selecting the desired spatial dose distribution involves balancing of conflicting goals. Specifically, increasing an intensity of a radiation dose increases the likelihood that the target area will be effectively treated. Nevertheless, increasing the intensity of the radiation dose also increases the likelihood that structures (e.g., organs and/or tissue) within the subject which are outside the target area may be damaged during treatment. As such, the process of selecting the desired spatial dose distribution involves balancing a desire to effectively treat the target area with a preference not to damage the structures outside the target area.

The structures within the subject may be either parallel-type structures or serial-type structures. Parallel-type structures are those structures in which a function of the structure may be preserved even when a portion of the structure is damaged. In contrast, serial-type structures are those structures in which the function of the structure may not be preserved when any portion of the structure is damaged. For example, a lung may be a parallel-type structure, and a spinal cord may be a serial-type structure.

In radiation therapy treatment plans, and particularly in computer aided treatment plans, it may be desirable to characterize an effect of the spatial dose distribution as a single number. One conventional method for characterizing the effect of the spatial dose distribution as a single number is an equivalent uniform dose ("EUD"). The EUD may be defined as a uniform dose distribution that would lead to the same effect as a given non-uniform, spatial dose distribution. Further, each structure within the subject may have an associated EUD tolerance, and there are numerous conventional methods for determining the EUD tolerance associated with a particular structure within the subject. When an EUD associated with an amount of radiation received by a particular structure is less than or equal to an EUD tolerance associated with the particular structure, the function of the particular structure would likely be preserved. Nevertheless, when the EUD associated with the amount of radiation received by the particular structure is greater than the EUD tolerance associated with the particular structure, the function of the particular structure may not be preserved.

In conventional radiation therapy treatment plans employing EUD, the actual EUD tolerances of those structures which a doctor determines can be adversely affected by radiation transmitted to the target area are used to determine a single, combined EUD tolerance value associated with these structures. Nevertheless, in such conventional radiation therapy treatment plans, the actual EUD tolerance of each structure within the subject may be different than the combined EUD tolerance, e.g., the EUD tolerance of a particular-structure within the subject may be less than or equal to the combined EUD tolerance.

In these conventional systems, a physician may select a desired EUD associated with radiation to be received by the target area, and a computer system may determine the amount of radiation for transmission to the target area based on the desired EUD, e.g., an intensity and/or a direction of the radiation beams which will achieve the desired EUD in the target area. Moreover, if the combined EUD is greater than or equal to an EUD associated with a portion of the desired amount of radiation which a structure would receive, the desired amount of radiation is transmitted to the target area. The determination of whether to transmit the desired amount of radiation to the target area is made independent of the actual EUD tolerance associated with the structure. Nevertheless, if the desired amount of radiation is transmitted to the target area, and the actual EUD tolerance associated with the structure is less than the EUD associated with the portion of the radiation which the structure receives, the function of the particular structure may not necessary be preserved.

SUMMARY OF THE INVENTION

Therefore, a need has arisen to provide arrangements and methods for treating a subject which overcome the above-described and other shortcomings of the related art.

One of the advantages of the present invention is that arrangements and methods are provided in which an application of a particular amount of energy (e.g., iteratively simulates different beams of radiation beams having varying intensities and/or direction) upon a target area or target areas (e.g., a cancer or a tumor) within a subject is simulated. For example, when energy (e.g., radiation) is transmitted to the target area, a portion of the energy may be received by structures (e.g., organs or parts thereof) within the subject which are outside the target area. When the simulation indicates that an equivalent uniform dose ("EUD") associated with a portion of the energy received by a particular structure is greater than a dose tolerance associated with the particular structure, a function of the particular structure may not be preserved.

Consequently, when simulating the application of the amount of energy upon the target area, it is possible to determine whether the EUD associated with the portion of the energy which the particular structure would receive is greater than the dose tolerance of the particular structure. This individual determination can be made for any number of structures within the subject. If the EUD associated with the portion of the energy which the particular structure would receive is greater than the dose tolerance of the particular structure, an application of a further amount of energy, e.g., a lesser amount of energy, can be simulated in which an intensity of at least some of the radiation beams are reduced. For example, the computer system can use a projection onto convex sets procedure to determine an appropriate further amount of energy. The simulation can continue until an optimum amount of energy to be applied to the target area, e.g., the greatest amount of energy is determined, which can be transmitted to the target area while also preserving the function of each of the structures. For example, the energy may include a plurality of radiation beams, and each of the radiation beams may have an associated intensity. Further, some of the radiation beams may only affect the particular structure, and some of the radiation beams may only affect a different structure, such that the intensity of each of the radiation beams can be adjusted based on EUD tolerance of the structure which they affect.

According to an exemplary embodiment of the present invention, an arrangement and method simulate an application of a particular amount of energy (e.g., radiation having a plurality of radiation beams) upon a target area or target areas (e.g., a cancer or a tumor) within a subject, in which a first structure (e.g., an organ) within the subject receives a first portion of the particular amount of energy, and a second structure within the subject receives a second portion of the particular amount of energy. A determination can also be made as to whether a first equivalent uniform dose ("EUD") associated with the first portion of the particular amount of energy received by the first structure is greater than a first dose tolerance (e.g., EUD tolerance) associated with the first structure. It can also be determined as to whether a second EUD associated with the second portion of the particular amount of energy received by the second structure is greater than a second dose tolerance associated with the second structure.

In another exemplary embodiment, an application of a further amount of energy (e.g., an amount of energy which is different than the particular amount of energy, having different radiation beam intensities and/or directions) is simulated upon the target area, in which the first structure receives a first portion of the further amount of energy, and the second structure receives a second portion of the further amount of energy. It is also determined as to whether a third EUD associated with the first portion of the further amount of energy received by the first structure is greater than the first dose tolerance, and whether a fourth EUD associated with the second portion of the further amount of energy received by the second structure is greater than the second dose tolerance. For example, a projection onto convex sets ("POCS") procedure can be used to determine an appropriate further amount of energy to be applied to the target area during the simulation.

Moreover, an intensity of the further amount of energy relative to an intensity of the particular amount of energy may depend on the above-described determinations. For example, an intensity of the first portion of the further amount of energy may be less than an intensity of the first portion of the particular amount of energy when the first EUD is greater than the first EUD tolerance by a predetermined amount. Similarly, an intensity of the second portion of the further amount of energy can be less than an intensity of the second portion of the particular amount of energy when the second EUD is greater than the second EUD tolerance by the predetermined amount. In contrast, the intensity of the first portion of the further amount of energy may be greater than the intensity of the first portion of the particular amount of energy when the first EUD is less than the first EUD tolerance by the predetermined amount. Similarly, the intensity of the second portion of the further amount of energy can be greater than the intensity of the second portion of the particular amount of energy when the second EUD is less than the second EUD tolerance by the predetermined amount. Moreover, the intensity of the first portion of the further amount of energy may be equal to the intensity of the first portion of the particular amount of energy when the first EUD is within the predetermined range of the first EUD tolerance. Similarly, the intensity of the second portion of the further amount of energy can be equal to the intensity of the second portion of the particular amount of energy when the second EUD is within the predetermined range of the second EUD tolerance.

In yet another exemplary embodiment of the present invention, data is forwarded to, e.g., to a distribution assembly. This data is associated with a resultant amount of energy for an application to the target area when at least one of the first EUD and the third EUD is within a predetermined range of the first EUD tolerance, and at least one of the second EUD and the fourth EUD is within the predetermined range of the second EUD tolerance. Moreover, the distribution assembly may transmit the resultant amount of energy to the target area. For example, the energy can include radiation, and the radiation can include at least one first radiation beam and at least one second radiation beam. Further, an intensity of the at least one first radiation beam may be associated with at least one of the first EUD and the third EUD, and an intensity of the at least one second radiation beam can be associated with at least one of the second EUD and the fourth EUD.

BRIEF DESCRIPTION OF THE DRAWINGS

For a more complete understanding of the present invention, the needs satisfied thereby, and the objects, features, and advantages thereof, reference now is made to the following descriptions taken in connection with the accompanying drawings.

DETAILED DESCRIPTION

Exemplary embodiments of the present invention and their advantages may be understood by referring to FIGS. 1–8, like numerals being used for like corresponding parts in the various drawings.

Figure 1:
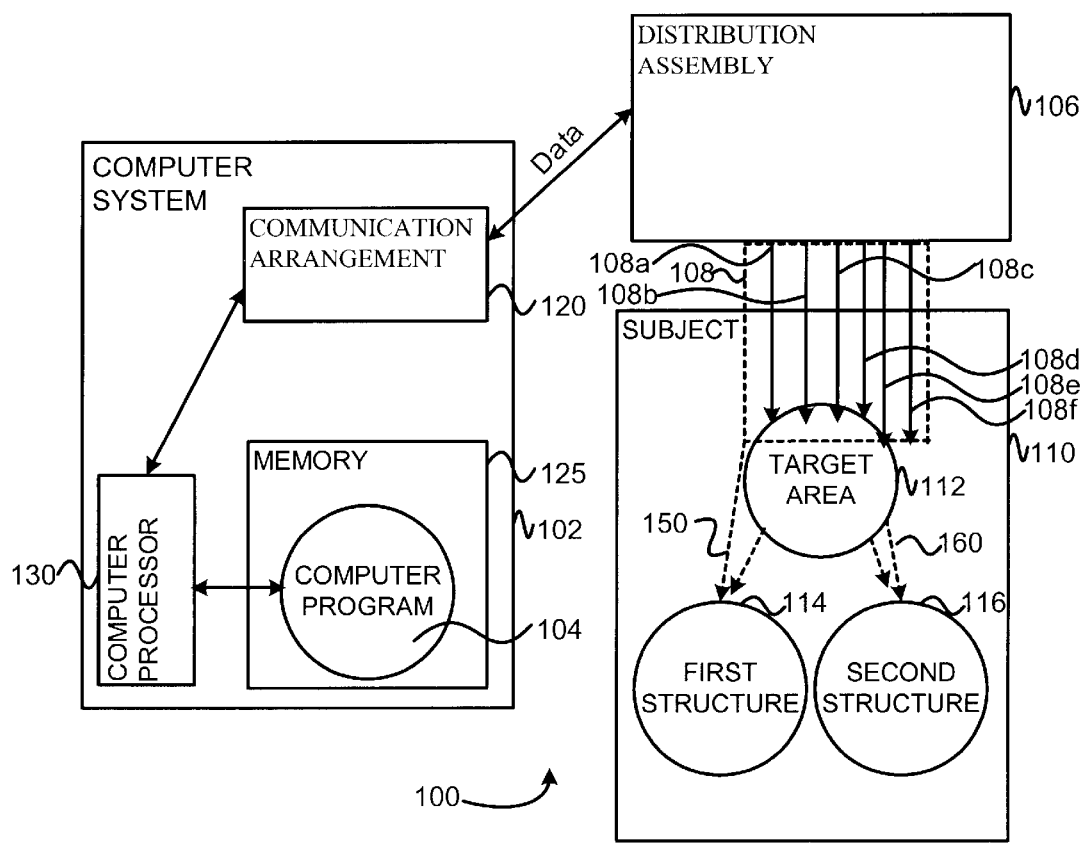
FIG. 1 is a schematic diagram of an exemplary embodiment of an arrangement according to the present invention.

Referring to FIG. 1, an exemplary embodiment of an arrangement 100 according to the present invention for treating a subject (e.g., using radiotherapy) is provided. The arrangement 100 may include a computer system 102. A computer program 104 can be stored in a storage arrangement 125 (e.g., a memory, a hard-drive, etc.). The computer system 102 also can include a computer processor 130 adapted to be in communication with the computer program 104, and a communication arrangement 120 adapted to be in communication with the computer processor 130. When the computer system 102 is executing the computer program 104, the computer system 102 can be adapted to simulate an application of a first amount of energy (e.g., radiation beams 108 having a first plurality of radiation beams 108a–108c and a second plurality of radiation beams 108d–108g) upon at least one target area 112 (e.g., a cancer or a tumor) within a subject 110. For the target area 112, a first structure 114 (e.g., an organ, such as a serial-type or parallel-type organ) that is located within the subject 110 receives a first portion 150 of the first amount of energy, and a second structure 116 located within the subject 110 receives a second portion 160 of the first amount of energy. The computer system 102 may also be adapted to determine whether an equivalent uniform dose ("EUD") associated with the first portion 150 of the first amount of energy received by the first structure 114 is greater than a dose tolerance (e.g., EUD tolerance) associated with the first structure 114. The computer system may further be adapted to determine whether an EUD associated with the second portion 160 of the first amount of energy received by the second structure 116 is greater than a dose tolerance associated with the second structure 116. Although FIG. 1 depicts a first structure 114 and a second structure 116, it should be understood by those of ordinary skill in the art that the arrangement 100 may be used in combination with any number of structures.

Specifically, if the EUD associated with the first portion 150 of the first amount of energy received by the first structure 114 is greater than the dose tolerance associated with the first structure 114, the transmission of the first amount of energy to the target area 112 may damage the first structure 114, such that a function of the first structure 114 may not be preserved. In such case, it may be desirable to reduce an intensity of the portion of the first amount of energy which affects the first structure 114. Similarly, if the EUD associated with the second portion 160 of the first amount of energy received by the second structure 116 is greater than the dose tolerance associated with the second structure 116, the transmission of the first amount of energy to the target area 112 may damage the second structure 116, such that a function of the second structure 116 may not be preserved. In such case, it may also be desirable to reduce an intensity of the portion of the first amount of energy which affects the second structure 116. In contrast, if the EUD associated with the first portion 150 of the first amount of energy received by the first structure 114 is less than or equal to the dose tolerance associated with the first structure 114, the transmission of the first amount of energy to the target area 112 likely will not damage the first structure 114.

For such case, the first amount of energy may not be sufficient to treat the target area 112, and it may be possible to increase the amount of energy transmitted to the target area 112 without damaging the first structure 114. Similarly, if the EUD associated with the second portion 160 of the first amount of energy received by the second structure 116 is less than or equal to the dose tolerance associated with the second structure 116, the transmission of the first amount of energy to the target area 112 will likely not damage the second structure 116. In this manner, the first amount of energy may not be sufficient to treat the target area 112, and it may be possible to increase the energy transmitted to the target area 112 without damaging the second structure 116.

Consequently, in another exemplary embodiment of the present invention, the computer system 102 may further be adapted to iteratively simulate the application of multiple amounts of energy upon the target area 112 in order to find an optimum balance between a preference to transmit as much energy to the target area 112 as possible, while preserving the function and integrity of the first structure 114 and the second structure 116, respectively. For example, when the computer system 102 is executing the computer program 104, the computer system 102 can be adapted to simulate the application of a second amount of energy upon the target area 112, in which the first structure 114 receives a first portion 150 of the second amount of energy, and the second structure 116 receives a second portion 160 of the second amount of energy. The computer system 102 may also be adapted to determine whether an EUD associated with the first portion 150 of the second amount of energy received by the first structure 114 is greater than the dose tolerance associated with the first structure 114. The computer system may further be adapted to determine whether an EUD associated with the second portion 160 of the second amount of energy received by the second structure 116 is greater than the dose tolerance associated with the second structure 116. Moreover, as discussed in more detail with respect to FIGS. 2 and 3, an exemplary embodiment of the present invention can utilize a projection onto convex sets ("POCS") procedure to determine or select an appropriate second amount of energy for simulation upon the target area 112. Moreover, the intensity and/or direction of the energy simulated upon the target area 112 may be adjusted based on the solution determined using the POCS procedure.

Moreover, the intensity of the second amount of energy relative to the intensity of the first amount of energy may depend on whether the EUD associated with the first portion 150 of the first amount of energy is greater than the EUD tolerance associated with the first structure 114, and/or whether the EUD associated with the second portion 160 of the first amount of energy is greater than the EUD tolerance associated with the second structure 116. For example, the intensity of the first portion 150 of the second amount of energy may be less than the intensity of the first portion 150 of the first amount of energy when the EUD associated with the first portion 150 of the first amount of energy is greater than the EUD tolerance associated with the first structure 114 by a predetermined amount. Similarly, the intensity of the second portion 160 of the second amount of energy can be less than the intensity of the second portion 160 of the first amount of energy when the EUD associated with the second portion 160 of the first amount of energy is greater than the EUD tolerance associated with the second structure 116 by the predetermined amount. In contrast, the intensity of the first portion 150 of the second amount of energy may be greater than the intensity of the first portion 150 of the first amount of energy when the EUD associated with the first portion 150 of the first amount of energy is less than the EUD tolerance associated with the first structure 114 by the predetermined amount. Similarly, the intensity of the second portion 160 of the second amount of energy can be greater than the intensity of the second portion 160 of the first amount of energy when the EUD associated with the second portion 160 of the first amount of energy is less than the EUD tolerance associated with the second structure 116 by the predetermined amount. Moreover, the intensity of the first portion 150 of the second amount of energy may be equal to the intensity of the first portion 150 of the first amount of energy when the EUD associated with the first portion 150 of the first amount of energy is within the predetermined range of the EUD tolerance associated with the first structure 114. In addition, the intensity of the second portion 160 of the second amount of energy can be equal to the intensity of the second portion 160 of the first amount of energy when the EUD associated with the second portion 160 of the first amount of energy is within the predetermined range of the EUD tolerance of the second structure 116.

It will be understood by those of ordinary skill in the art that the computer system 102 may be adapted to simulate the applications of the particular amounts of energy (e.g., a third amount of energy, a fourth amount of energy, a fifth amount of energy, etc.) upon the target area 112 until an optimum, (e.g., resultant) amount of energy to transmit to the target area 112 has been determined. For example, such optimum amount can be a maximum amount of energy which may be transmitted to the target area 112 without damaging the function or integrity of the first structure 114 and/or the second structure 116, respectively. For example, the computer system 102 can simulate applications of amounts of energy upon the target area 112 until the EUD associated with the first portion 150 of an Nth amount of energy received by the first structure 114, and until the EUD associated with the second portion 160 of the Nth amount of energy received by the second structure 116 are within a predetermined range of the EUD tolerance associated with the first structure 114 and the second structure 116, respectively. For example, the predetermined range can be between about 0.01 Gy and about 1.0 Gy, and the predetermined amount can be greater than the predetermined range.

Moreover, when the optimum amount of energy for transmission to the target area 112 has been determined using the above-described simulation, the computer system 102 may be adapted to transmit data associated with the optimum amount of energy to, e.g., a distribution assembly 106. The distribution assembly may be adapted to transmit the optimum amount of energy to the target area 112. For example, the optimum amount of energy may include beams of radiation 108, and the beams of radiation 108 may include the first plurality of radiation beams 108a–108c, and the second plurality of radiation beams 108d14 108f. The intensity and/or direction of each of the beams of radiation 108 may be selected based on the optimum amount of energy to be transmitted to the target area 112. For example, when the EUD tolerance associated with the first structure 114 is less than the EUD tolerance associated with the second structure 116, the intensity of the first radiation beams 108a–108c may be less than the intensity of the second radiation beams 108d–108f. Similarly, when the EUD tolerance associated with the first structure 114 is greater than the EUD tolerance associated with the second structure 116, the intensity of the first radiation beams 108a–108c may be greater than the intensity of the second radiation beams 108d–108f.

In any of the above-described embodiments of the present invention, the computer system 102 may be adapted to determine the further amounts of radiation to be simulated upon the target area, (e.g., the second amount of radiation, the second amount of radiation, etc.) using a projection onto convex sets ("POCS") procedure. Specifically, the EUD may be expressed by the formula:

$$EUD = \left(\frac{1}{N}\sum_{i=1}^{N} D_i^a\right)^{1/a}$$

in which (a) is a tissue specific parameter which is negative for tumors and/or cancers, and is positive for the first structure 112 and/or the second structure 114, (D) is a dose distribution within one of the structures 112 and 114, and (N) is a number of dimensions of the dose distribution (D).

For example, the first structure 114 and the second structure 116 within the subject 110 may be either parallel-type structures or serial-type structures. Parallel-type structures are those structures in which a function of the structure may be preserved even when a portion of the structure is damaged. In contrast, serial-type structures are those structures in which the function of the structure may not be preserved when any portion of the structure is damaged. A lung may be a parallel-type structure, and a spinal cord can be a serial-type structure. Moreover, for parallel-type structures the tissue specific parameter (a) may be about 1, and for serial-type structures the tissue specific parameter (a) may be greater than 1. For example, the tissue specific parameter (a) for the spinal cord may be about 7.4.

Figure 5:
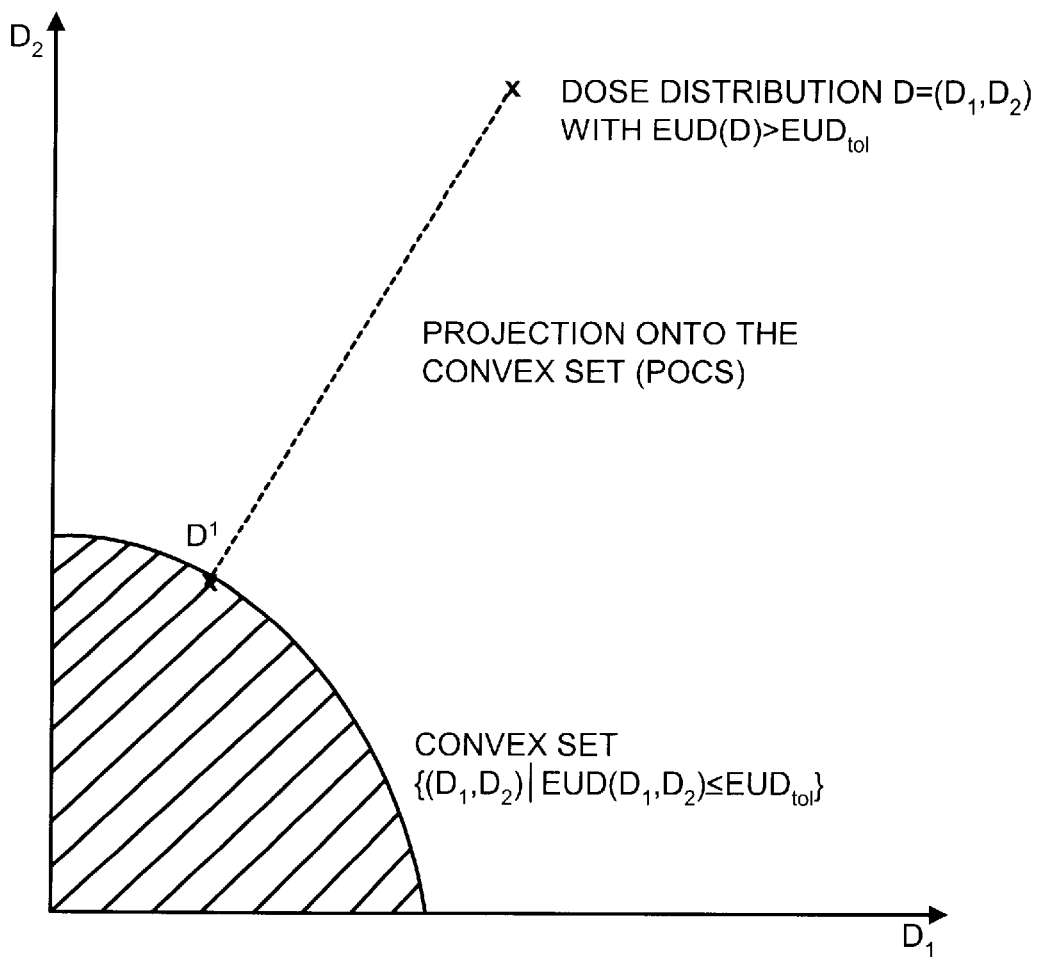
FIG. 5 is a graph of an exemplary projected dose distribution for a two-dimensional dose distribution implemented by the exemplary embodiments of the arrangement and method of the present invention.

Dose distributions (D) within a particular structure are generally based the amount of energy and the direction that the energy is applied, e.g., based on radiation beam intensity and/or radiation beam direction. Accordingly, with respect to the first structure 114, substantially most if not all dose distributions (D) within the first structure 114 that have an associated EUD which is less than or equal to the EUD tolerance associated with the first structure 114 form a convex or a constraint set inside a N-dimensional space. The POCS procedure operates to solve a constraint optimization problem by repeated projections onto the constraint set. For example, if the EUD associated with a particular dose distribution (D) within the first structure 114 is greater than the EUD tolerance of the first structure 114, the POCS procedure may be utilized to project a particular dose distribution (D) within the first structure 114 onto a set of dose distributions (D') within the first structure 114 having an associated EUD which is within the predetermined range of the EUD tolerance of the first structure 114. Specifically, the POCS procedure may be used to determine the dose distribution (D') within the first structure 114 which is closest to the particular dose distribution (D) within the first structure 114, and which fulfills the constraint set. Moreover, a shape of the constraint set may depend on the tissue specific parameter (a) and the EUD tolerance of the first structure. FIG. 5 depicts an exemplary projected dose distribution (D') within the first structure 114 for a two dimensional dose distribution (D) according to the present invention.

In order to determine the dose distribution (D'), the POCS procedure may evaluate the following two equations:

$$EUD_{tot} = \left(\frac{1}{N}\sum_{i=1}^{N} D_i'^a\right)^{1/a}; \quad \text{and}$$

$$\sum_{i=1}^{N}(D_i - D_i')^2 = f(D') = \min.$$

The definition of a Lagrange function $L(D',\lambda)=f(D')+\lambda \cdot [EUD_{tol}-EUD(D')]$, and the setting of the partial derivative of L with respect to D' equal to zero, leads to the requirement that $$\frac{D_j - D_j'}{D_j'^{(a-1)}} = \text{const., in which } j = 1, \ldots, N.$$

One solution for this equation which is likely to be exact for a=1 and a=2, and that is approximately exact for any other value for a is $$\frac{D_j - D_j'}{D_j'^{(a-1)}} \approx \frac{EUD - EUD_{tot}}{EUD_{tot}^{(a-1)}}.$$

During the optimization, this equation may be iteratively solved so as to obtain the explicit values of $D'_j$, and some or all of the radiation beam 108 intensities can be adjusted based on the solution. Moreover, this equation provides an implicit definition of a projected dose in each voxel, e.g., structure, j.

Figure 6:
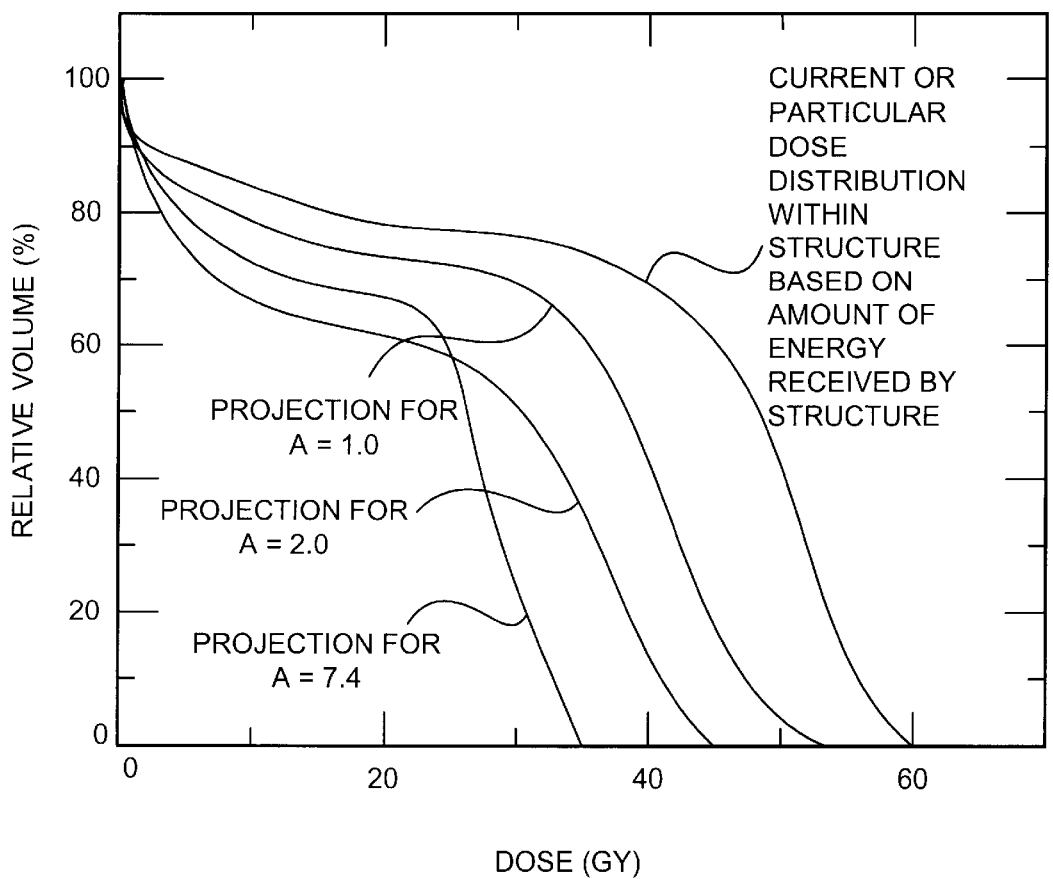
FIG. 6 is a first example of a dose volume histogram of a particular dose distribution within a particular structure, and projected dose distributions within the particular structure for various tissue specific parameters.
Figure 7:
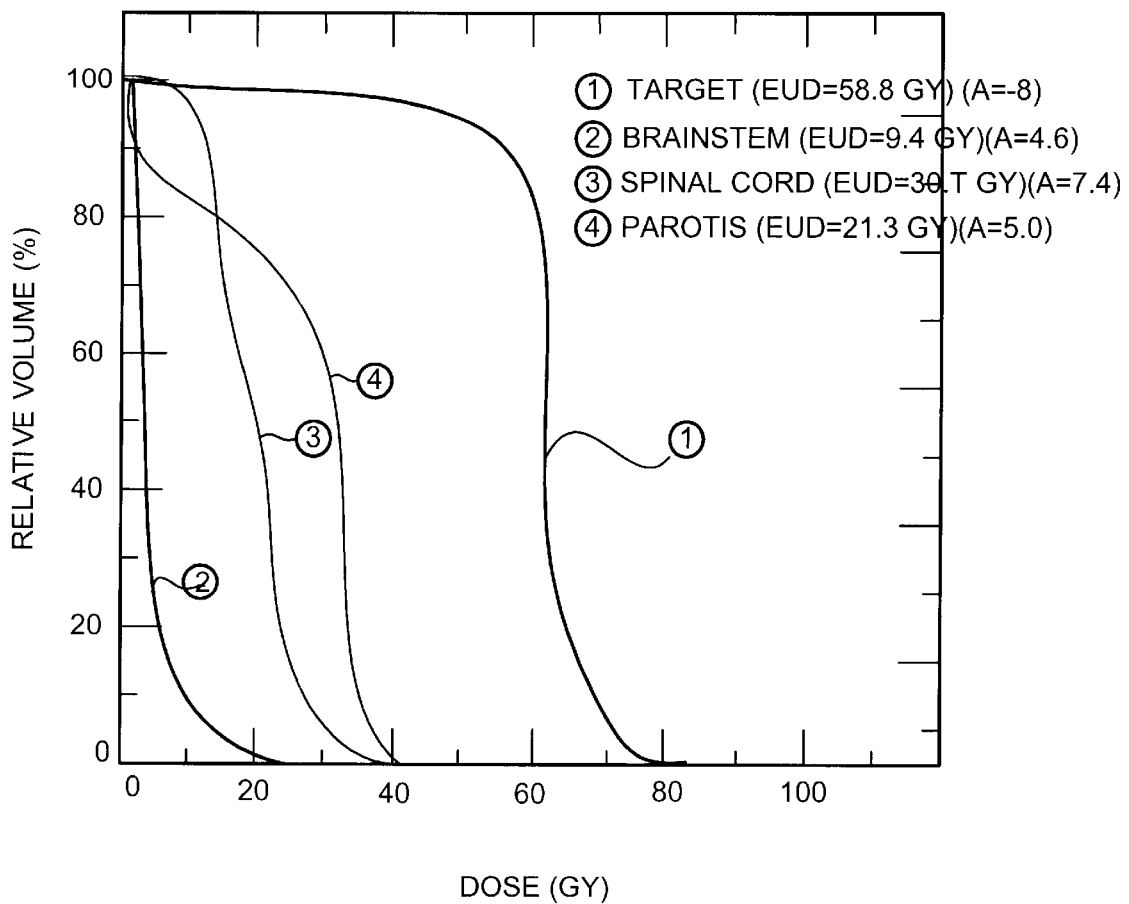
FIG. 7 is a second example of a dose volume histogram of a particular dose distribution within particular structures, and projected dose distributions within the particular structures for various tissue specific parameters.
Figure 8:
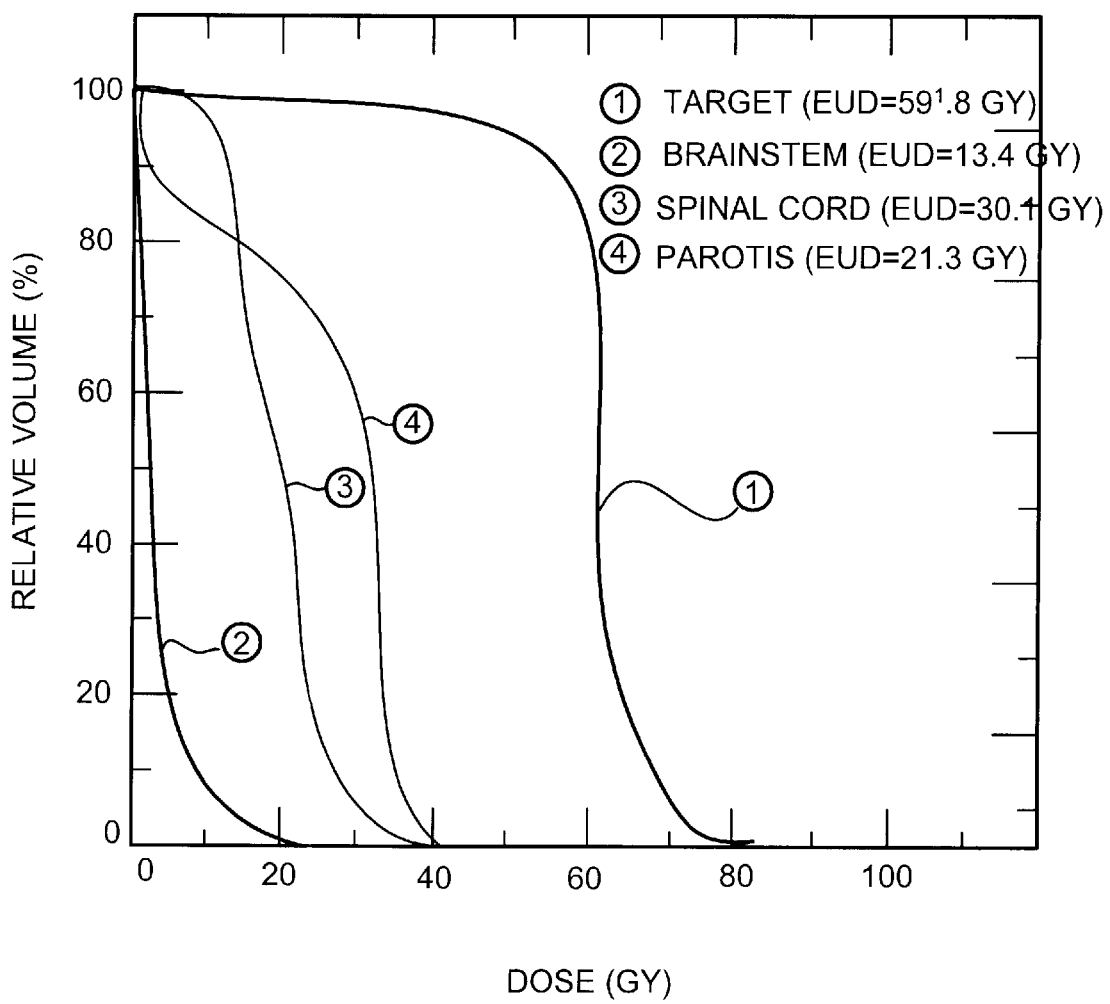
FIG. 8 is a third example of a dose volume histogram of a particular dose distribution within particular structures, and projected dose distributions within the particular structures for various tissue specific parameters.

Referring to FIG. 6, an example of a dose volume histogram ("DVH") of a particular dose distribution (D) within a structure at risk, and projected dose distributions (D') of the particular dose distribution (D) for exemplary values of (a) associated with the structure at risk are depicted. In this exemplary illustration, tissue specific parameters (a) are selected as a=1, a=2, and a=7.4, and the EUD associated with the particular dose distribution (D) within the structure at risk was determined to be 40.9 Gy, 45.4 Gy, and 50.8 Gy, respectively. Further, the EUD tolerance is selected as 33 Gy for each value of (a). In addition, the POCS procedure has been performed to obtain a dose distribution for a=1, a=2, and a=7.4 which satisfied the constraint set. Nevertheless, it will be understood by those in ordinary skill in the art that in obtaining an actual projected dose distribution, it may not be possible to achieve the exact dose distribution obtained using the POCS procedure. Specifically, as shown in FIG. 6, the EUD associated with the projected dose distribution (D') within the structure at risk when a=1 was 34 Gy, the EUD associated with the projected dose distribution (D') within the structure at risk when a=2 was 32.99 Gy, and the EUD associated with the projected dose distribution (D') within the structure at risk when a=7.4 was 32.39 Gy. It should be understood by those of ordinary skill in the art that for a=1, the constraint is substantially fulfilled but may not be necessarily exactly fulfilled. Nevertheless, the constraint is within the predetermined range. Moreover, FIGS. 7 and 8 illustrate examples of DVH's of particular dose distributions (D) within a brainstem, a spinal cord, and a parotis.

Figure 2:
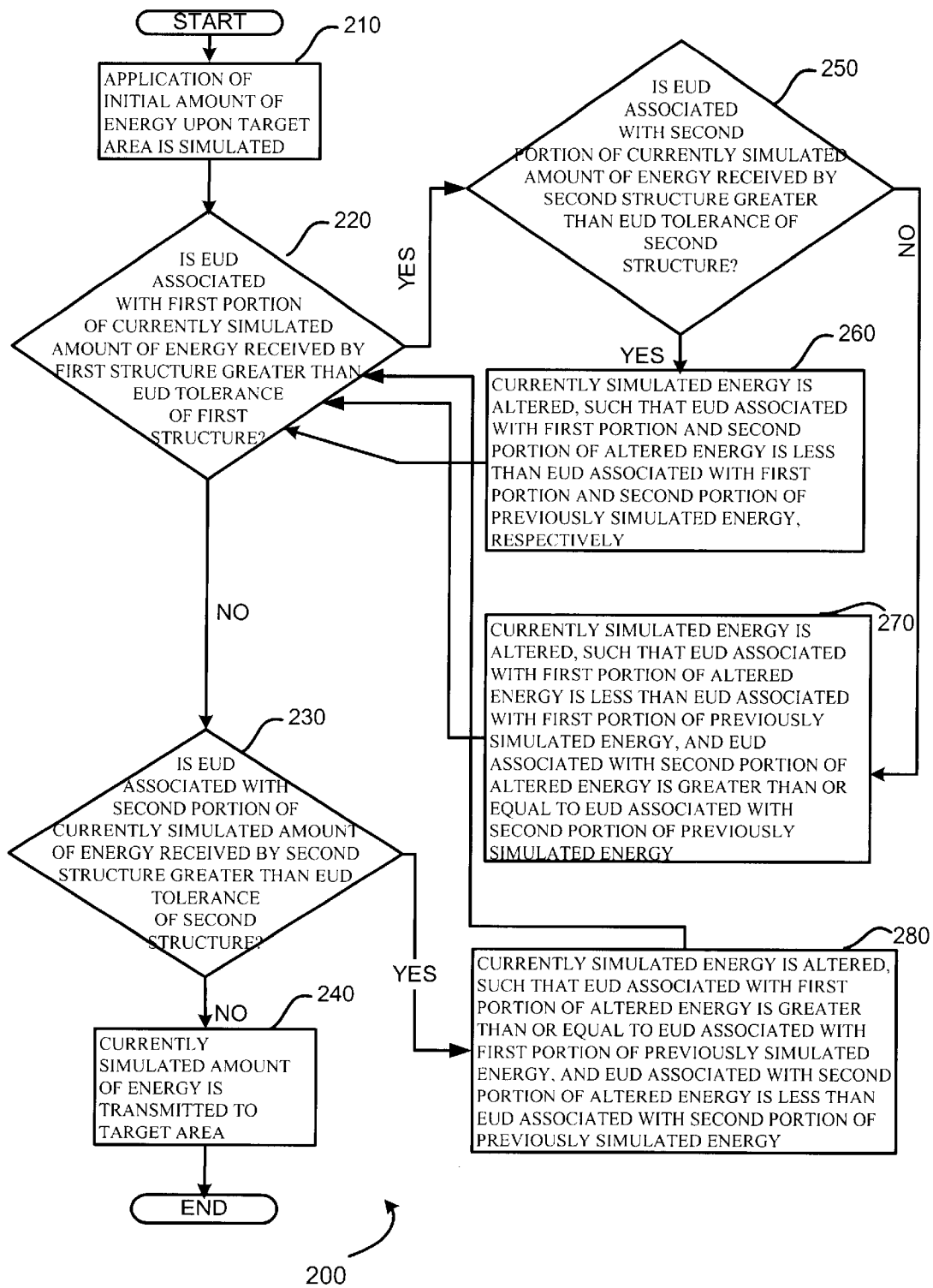
FIG. 2 is a flow diagram of a first exemplary embodiment of a method for treating a subject according to the present invention.

FIG. 2 shows a flow diagram of a first exemplary embodiment of a method 200 which can be used by the arrangement of FIG. 1. In step 210 of this exemplary method, the application of an initial (e.g., a desired or a particular) amount of energy upon the target site 112 is simulated. In step 220, the computer system 102 determines whether the EUD associated with the first portion 150 of a currently simulated amount of energy received by the first structure 114 is greater than the EUD tolerance associated with the first structure 114. For example, in the first iteration, the current amount of energy is the initial amount of energy which may be a starting point for the exemplary embodiment of the method 200. If the EUD associated with the first portion 150 of the currently simulated amount of energy received by the first structure 114 is not greater than the EUD tolerance associated with the first structure 114, then in step 230, the computer system 102 is adapted to determine whether the EUD associated with the second portion 160 of the currently simulated amount of energy received by the second structure 116 is greater than the EUD tolerance associated with the second structure 116. If the EUD associated with the second portion 160 of the currently simulated amount of energy received by the second structure 14 is not greater than the EUD tolerance associated with the second structure 116, then in step 240, the currently simulated amount of energy can be transmitted to the target area 112.

However, if in step 220 the EUD associated with the first portion 150 of the currently simulated amount of energy received by the first structure 114 is greater than the EUD tolerance associated with the first structure 114, the computer system 102 is adapted to determine whether the EUD associated with the second portion 160 of the currently simulated amount of energy received by the second structure 116 is greater than the EUD tolerance associated with the second structure 116 (step 250). If the EUD associated with the second portion 160 of the currently simulated amount of energy received by the second structure 116 is greater than the EUD tolerance associated with the second structure 116, then in step 260, the currently simulated amount of energy can be altered. For example, such alteration can be accomplished so that the EUD associated with the first portion 150 of the altered amount of energy and the EUD associated with the second portion 160 of the altered amount of energy are less than the EUD associated with the first portion 150 of the previously simulated amount of energy (e.g., during the first iteration, the initially simulated amount of energy) and the second portion 160 of the previously simulated amount of energy. The currently simulated amount of energy may be altered using the POCS procedure to obtain a dose distribution which satisfies the constraint set. Moreover, the altered amount of energy becomes the currently simulated amount of energy (e.g., a second iteration begins), and the processing is forwarded back to step 220 and the procedure thereof is repeated for the new currently simulated amount of energy.

If in step 250 the EUD associated with the second portion 160 of the currently simulated amount of energy received by the second structure 116 is not greater than the EUD tolerance associated with the second structure 116, then in step 270, the currently simulated amount of energy is altered such that the EUD associated with the first portion 150 of the altered amount of energy is less than the EUD associated with the first portion 150 of the previously simulated amount of energy (e.g., during the first iteration, the initially simulated amount of energy). The currently simulated amount of energy is also altered such that the EUD associated with the second portion 160 of the altered amount of energy is greater than or equal to the EUD associated with the second portion 160 of the previously simulated amount of energy. For example, the currently simulated amount of energy may be altered using the POCS procedure to obtain a dose distribution which satisfies the constraint set. As described above, the altered amount of energy becomes the currently simulated amount of energy (e.g., the second iteration begins), and the processing is forwarded back to step 220 to be repeated for the new currently simulated amount of energy.

Nevertheless, if in step 230 the EUD associated with the second portion 160 of the currently simulated amount of energy received by the second structure 114 is greater than the EUD tolerance associated with the second structure 116, then in step 280, the currently simulated amount of energy is altered such that the EUD associated with the first portion 150 of the altered amount of energy is greater than or equal to the EUD associated with the first portion 150 of the previously simulated amount of energy (e.g., again during the first iteration, the initially simulated amount of energy). The currently simulated amount of energy is also altered such that the EUD associated with the second portion 160 of the altered amount of energy is less than the EUD associated with the second portion 160 of the previously simulated amount of energy. Similarly to the above description, the currently simulated amount of energy may be altered using the POCS procedure to obtain a dose distribution which satisfies the constraint set. The altered amount of energy becomes the currently simulated amount of energy (e.g., the second iteration begins). Then, the processing is forwarded to step 220 to be repeated for the new currently simulated amount of energy. It should be understood by those of ordinary skill in the art that the method 200 may continue for a number of iterations until the EUD associated with the first portion 150 and the second portion 160 of the most recently simulated amount of energy is less than or equal to the EUD tolerance associated with the first structure 114 and the second structure 116, respectively. Moreover, the method 200 may be employed using the above-described predetermined range for the comparison between the EUDs and the particular EUD tolerances.

Figure 3:
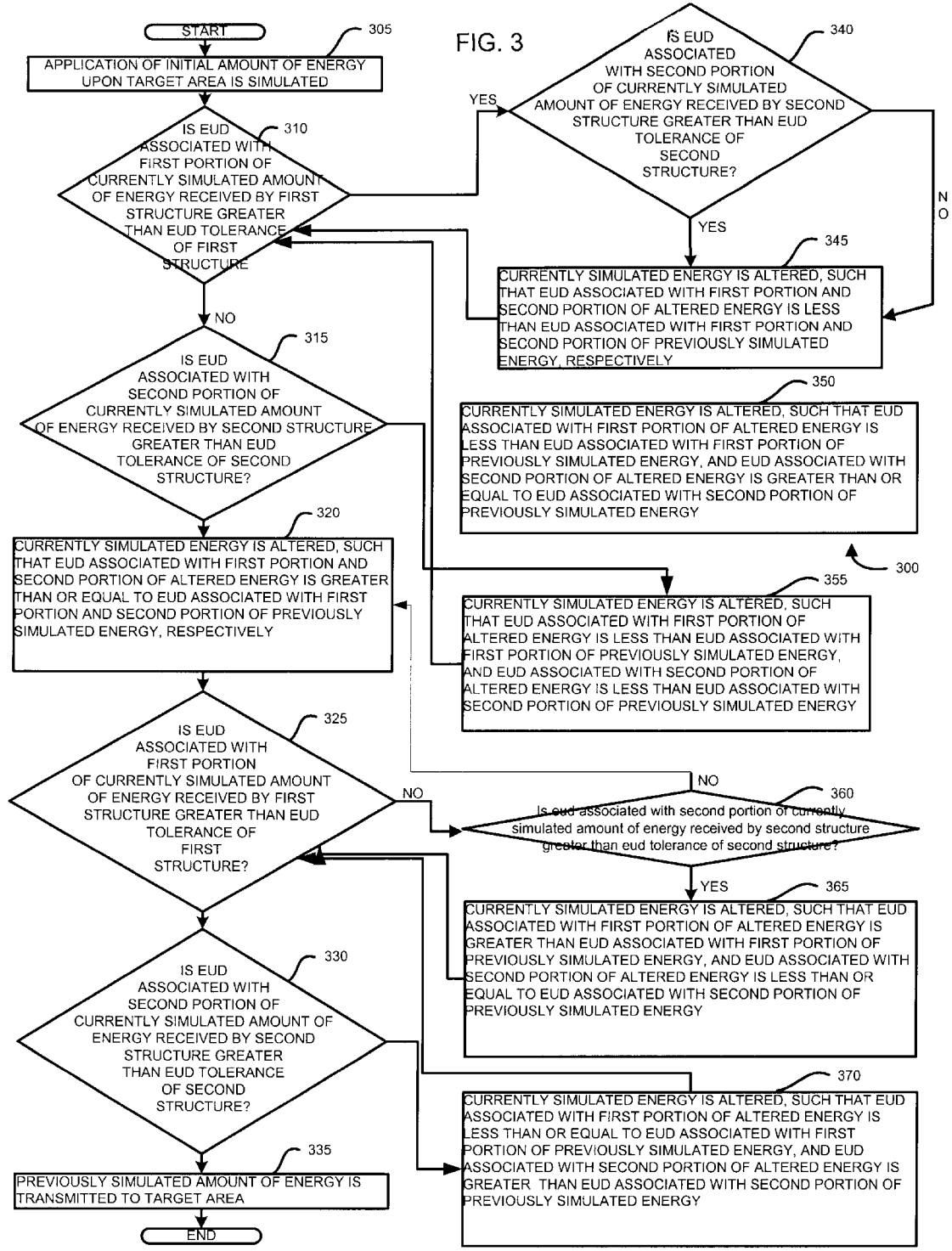
FIG. 3 is a flow diagram depicting an exemplary variation of the method shown in FIG. 2.

Referring to FIG. 3, a flow diagram of a second exemplary embodiment of a method 300 according to the present invention is illustrated, which is a variation of the method 200 of FIG. 2. In the exemplary method 300, the steps 305, 310, 315, 340, 345, 350, and 355, substantially correspond to steps 210, 220, 230, 250, 260, and 270 of FIG. 2, respectively. Therefore, steps 305, 310, 315, 340, 345, 350, and 355 are not discussed in further detail herein below. However, step 240 of the exemplary method 200 can be replaced by steps 320, 325, 330, 335, 360, 365, and 370. Specifically, even when the EUD associated with the first portion 150 and the second portion 160 of the most recently simulated amount of energy is less than or equal to the EUD tolerance associated with the first structure 114 and the second structure 116, respectively, it may be desirable to increase the most recently simulated amount of energy in order to optimize the amount of energy which may be transmitted to the target area 112. Consequently, in step 320, when the EUD associated with the first portion 150 and the second portion 160 of the most recently simulated amount of energy is less than or equal to the EUD tolerance associated with the first structure 114 and the second structure 116, respectively, the currently simulated amount of energy can be altered. Specifically, the currently simulated amount of energy is altered such that the EUD associated with the first portion 150 of the altered amount of energy and the EUD associated with the second portion 160 of the altered amount of energy are greater than or equal to the EUD associated with the first portion 150 of the previously simulated amount of energy and the second portion 160 of the previously simulated amount of energy, respectively. For example, the currently simulated amount of energy may be altered using the POCS procedure to obtain a greater dose distribution which satisfies the constraint set.

In step 325, the altered amount of energy becomes the current amount of energy (i.e., the second iteration begins). Moreover, the computer system 102 is adapted to determine whether the EUD associated with the first portion 150 of the currently simulated amount of energy received by the first structure 114 is greater than the EUD tolerance associated with the first structure 114. If the EUD associated with the first portion 150 of the currently simulated amount of energy received by the first structure 114 is greater than the EUD tolerance associated with the first structure 114, then in step 330, the computer system 102 determines whether the EUD associated with the second portion 160 of the currently simulated amount of energy received by the second structure 116 is greater than the EUD tolerance associated with the second structure 116. If the EUD associated with the second portion 160 of the currently simulated amount of energy received by the second structure 114 is greater than the EUD tolerance associated with the second structure 116, the previously simulated amount of energy (e.g., the amount of energy which was simulated prior to being altered in step 320) can be transmitted to the target area 112.

If, however, in step 325 the EUD associated with the first portion 150 of the currently simulated amount of energy received by the first structure 114 is not greater than the EUD tolerance associated with the first structure 114, the method 300 proceeds to step 360 in which, the computer system 102 determines whether the EUD associated with the second portion 160 of the currently simulated amount of energy received by the second structure 116 is greater than the EUD tolerance associated with the second structure 116. If the EUD associated with the second portion 160 of the currently simulated amount of energy received by the second structure 116 is greater than the EUD tolerance associated with the second structure 116, then in step 365, the currently simulated amount of energy is altered. Specifically, the currently simulated amount of energy is altered such that the EUD associated with the first portion 150 of the altered amount of energy is greater than the EUD associated with the first portion 150 of the previously simulated amount of energy, and the second portion 160 of the altered amount of energy is less than or equal to the EUD associated with the second portion 160 of the previously simulated amount of energy. For example, the currently simulated amount of energy may be altered using the POCS procedure to obtain a dose distribution which satisfies the constraint set. The altered amount of energy becomes the currently simulated amount of energy (e.g., a third iteration begins), and the processing is forwarded to step 325 to be repeated for the new currently simulated amount of energy.

If, in step 360, the EUD associated with the second portion 160 of the currently simulated amount of energy received by the second structure 116 is not greater than the EUD tolerance associated with the second structure 116, the processing of the exemplary method 300 is forwarded back to step 320 for another alteration of the currently simulated amount of energy. However, if in step 330 the EUD associated with the second portion 160 of the currently simulated amount of energy received by the second structure 116 is not greater than the EUD tolerance associated with the second structure 116. Then, in step 370, the currently simulated amount of energy is altered such that the EUD associated with the first portion 150 of the altered amount of energy is less than or equal to the EUD associated with the first portion 150 of the previously simulated amount of energy, and the second portion 160 of the altered amount of energy is greater than the EUD associated with the second portion 160 of the previously simulated amount of energy. For example, the currently simulated amount of energy may be altered using the POCS procedure to obtain a dose distribution which satisfies the constraint set. Then the processing is forwarded to step 325, and the altered amount of energy becomes the currently simulated amount of energy (e.g., a third iteration begins), and step 325 is repeated for the new currently simulated amount of energy. It should be understood by those of ordinary skill in the art that the method 200 may be employed using the above-described predetermined range for the comparison between the EUD and the EUD tolerance.

Figure 4:
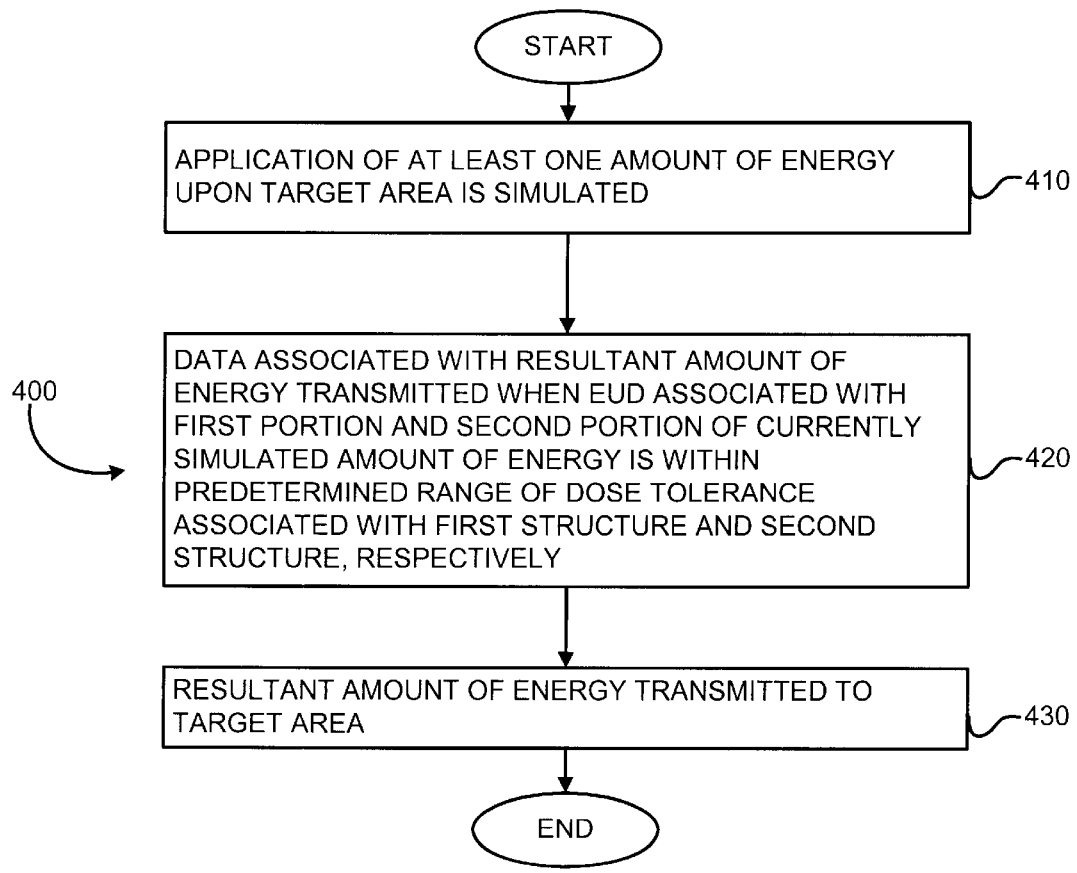
FIG. 4 is a flow diagram of a second exemplary embodiment of the method for treating a subject according to the present invention.

Referring to FIG. 4, a flow diagram of a second exemplary embodiment of a method 400 which can be used by the arrangement of FIG. 1 is depicted. In step 410, the application of at least one particular amount of energy upon a target area is simulated. For example, the exemplary method 200 and/or the exemplary method 300 may be used for such purpose. In step 420, data associated with a resultant amount of energy is transmitted (e.g., to the distribution assembly 106) when the EUD associated with the first portion 150 and the EUD associated with the second portion 160 of a currently simulated amount of energy is within the predetermined range of the dose tolerance associated with the first structure 114 and the dose tolerance associated with the second structure 116, respectively. Moreover, in step 430, the resultant amount of energy is transmitted to the target are 112.

While the invention has been described in connecting with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed is:

1. An arrangement, comprising:
   a computer system, wherein when executing a software program, the computer system is adapted to:
   simulate an application of a particular amount of energy upon a target area within a subject, wherein a first structure within the subject receives a first portion of the particular amount of energy, and a second structure within the subject receives a second portion of the particular amount of energy,
   determine whether a first equivalent uniform dose ("EUD") associated with the first portion of the particular amount of energy is greater than a first dose tolerance associated with the first structure, and
   determine whether a second EUD associated with the second portion of the particular amount of energy is greater than a second dose tolerance associated with the second structure.

2. The arrangement of claim 1, wherein the first dose tolerance is a first EUD tolerance associated with the first structure, wherein the second dose tolerance is a second EUD tolerance associated with the second structure, and wherein the first EUD tolerance is different than the second EUD tolerance.

3. The arrangement of claim 2, wherein the computer system is further adapted to:
   simulate an application of a further amount of energy upon the target area, wherein the first structure receives a first portion of the further amount of energy, and the second structure receives a second portion of the further amount of energy,
   determine whether a third EUD associated with the first portion of the further amount of energy is greater than the first EUD tolerance, and
   determine whether a fourth EUD associated with the second portion of the further amount of energy is greater than the second EUD tolerance.

4. The arrangement of claim 3, wherein the third EUD is less than the first EUD when the first EUD is greater than the first EUD tolerance by a predetermined amount.

5. The arrangement of claim 4, wherein the fourth EUD is less than the second EUD when the second EUD is greater than the second EUD tolerance by the predetermined amount.

6. The arrangement of claim 5, wherein the third EUD is greater than the first EUD when the first EUD is less than the first EUD tolerance by the predetermined amount.

7. The arrangement of claim 6, wherein the fourth EUD is greater than the second EUD when the second EUD is less than the second EUD tolerance by the predetermined amount.

8. The arrangement of claim 7, wherein the third EUD is equal to the first EUD when the first EUD is within a predetermined range of the first EUD tolerance, and wherein the fourth EUD is equal to the second EUD when the second EUD is within the predetermined range of the second EUD tolerance.

9. The arrangement of claim 8, wherein an intensity of the first portion of the further amount of energy is less than an intensity of the first portion of the particular amount of energy when the first EUD is greater than the first EUD tolerance by the predetermined amount, and wherein an intensity of the second portion of the further amount of energy is less than an intensity of the second portion of the particular amount of energy when the second EUD is greater than the second EUD tolerance by the predetermined amount.

10. The arrangement of claim 9, wherein the intensity of the first portion of the further amount of energy is greater than the intensity of the first portion of the particular amount of energy when the first EUD is less than the first EUD tolerance by the predetermined amount, and wherein the intensity of the second portion of the further amount of energy is greater than the intensity of the second portion of the particular amount of energy when the second EUD is less than the second EUD tolerance by the predetermined amount.

11. The arrangement of claim 10, wherein the intensity of the first portion of the further amount of energy is equal to the intensity of the first portion of the particular amount of energy when the first EUD is within the predetermined range of the first EUD tolerance, and wherein the intensity of the second portion of the further amount of energy is equal to the intensity of the second portion of the particular amount of energy when the second EUD is within the predetermined range of the second EUD tolerance.

12. The arrangement of claim 3, wherein a projection onto convex sets ("POCS") procedure is used to determine the further amount of energy.

13. The arrangement of claim 3, wherein the computer system is further adapted to transmit data associated with a resultant amount of energy for an application to the target area when:
   at least one of the first EUD and the third EUD is within a predetermined range of the first EUD tolerance, and
   at least one of the second EUD and the fourth EUD is within the predetermined range of the second EUD tolerance.

14. The arrangement of claim 13, wherein the computer system is further adapted to simulate an application of a certain amount of energy upon the target area when each of the first EUD and the third EUD is outside the predetermined range of the first EUD tolerance.

15. The arrangement of claim 13, wherein the computer system is further adapted to simulate an application of a certain amount of energy upon the target area when each of the second EUD and the fourth EUD is outside the predetermined range of the first EUD tolerance.

16. The arrangement of claim 13, wherein the predetermined range is between about 0.01 Gy and about 1 Gy, and wherein the particular amount is greater than the predetermined range.

17. The arrangement of claim 13, wherein a POCS procedure is used to determine the further amount of energy.

18. The arrangement of claim 17, wherein the POCS procedure is used to determine the certain amount of energy.

19. The arrangement of claim 13, wherein the computer system transmits the data to a distribution assembly.

20. The arrangement of claim 19, wherein the distribution assembly is adapted to transmit the resultant amount of energy to the target area.

21. The arrangement of claim 20, wherein the energy comprises radiation.

22. The arrangement of claim 21, wherein the radiation comprises at least one first radiation beam and at least one second radiation beam, wherein an intensity of the at least one first radiation beam is associated with at least one of the first EUD and the third EUD, and wherein an intensity of the at least one second radiation beam is associated with at least one of the second EUD and the fourth EUD.

23. The arrangement of claim 22, wherein the at least one first radiation beam comprises a first plurality of radiation beams, and wherein the at least one second radiation beam comprises a second plurality of radiation beams.

24. The arrangement of claim 1, wherein the first structure is a first organ and the second structure is a second organ.

25. The arrangement of claim 24, wherein the first organ is one of a first serial-type organ and a first parallel-type organ, and wherein the second organ is one of a second serial-type organ and a second parallel-type organ.

26. An arrangement, comprising:
   a computer system, wherein when executing a software program, the computer system is adapted to:
      simulate an application of a particular amount of energy upon a target area within a subject, wherein a first structure within the subject receives a first portion of the particular amount of energy, and a second structure within the subject receives a second portion of the particular amount of energy, and
      transmit data associated with a resultant amount of energy to be applied to the target area when:
         a first equivalent uniform dose ("EUD") associated with the first portion of the particular amount of energy is within a predetermined range of a first dose tolerance associated with the first structure, and
         a second EUD associated with the second portion of the particular amount of energy is within the predetermined range of a second dose tolerance associated with the second structure.

27. The arrangement of claim 26, wherein the first dose tolerance is a first EUD tolerance associated with the first structure, wherein the second dose tolerance is a second EUD tolerance associated with the second structure, and wherein the first EUD tolerance is different than the second EUD tolerance.

28. An arrangement, comprising:
   a computer system, wherein when executing a software program, the computer system is adapted to:
      simulate an application of a particular amount of energy upon a target area within a subject, wherein a first structure within the subject receives a first portion of the particular amount of energy,
      determine whether a first equivalent uniform dose ("EUD") associated with the first portion of the particular, amount of energy is greater than a first dose tolerance associated with the first structure, and
      determine a further amount of energy to be applied to the target area using a projection onto convex sets ("POCS") procedure.

29. The arrangement of claim 28, wherein the computer system is further adapted to simulate an application of the further amount of energy upon the target area, wherein the first structure receives a first portion of the further amount of energy, wherein a further structure within the subject receives a further portion of the first amount of energy and a second portion of the second amount of energy, and wherein the computer system is further adapted to determine whether a second EUD associated with the second portion of the particular amount of energy is greater than a second dose tolerance associated with the second structure.

30. The arrangement of claim 29, wherein the first dose tolerance is a first EUD tolerance associated with the first structure, wherein the second dose tolerance is a second EUD tolerance associated with the second structure, and wherein the first EUD tolerance is different than the second EUD tolerance.

31. The arrangement of claim 30, wherein the computer system is further adapted to:
   determine whether a third EUD associated with the first portion of the further amount of energy is greater than the first EUD tolerance, and
   determine whether a fourth EUD associated with the second portion of the further amount of energy is greater than the second EUD tolerance.

32. The arrangement of claim 31, wherein the third EUD is less than the first EUD when the first EUD is greater than the first EUD tolerance by a predetermined amount, and wherein the fourth EUD is less than the second EUD when the second EUD is greater than the second EUD tolerance by the predetermined amount.

33. The arrangement of claim 32, wherein the third EUD is greater than the first EUD when the first EUD is less than the first EUD tolerance by the predetermined amount, and wherein the fourth EUD is greater than the second EUD when the second EUD is less than the second EUD tolerance by the predetermined amount.

34. The arrangement of claim 33, wherein the third EUD is equal to the first EUD when the first EUD is within a predetermined range of the first EUD tolerance, and wherein the fourth EUD is equal to the second EUD when the second EUD is within the predetermined range of the second EUD tolerance.

35. The arrangement of claim 34, wherein an intensity of the first portion of the further amount of energy is less than an intensity of the first portion of the particular amount of energy when the first EUD is greater than the first EUD tolerance by the predetermined amount, and wherein an intensity of the second portion of the further amount of energy is less than an intensity of the second portion of the particular amount of energy when the second EUD is greater than the second EUD tolerance by the predetermined amount.

36. The arrangement of claim 35, wherein the intensity of the first portion of the further amount of energy is greater than the intensity of the first portion of the particular amount of energy when the first EUD is less than the first EUD tolerance by the predetermined amount, and wherein the intensity of the second portion of the further amount of energy is greater than the intensity of the second portion of the particular amount of energy when the second EUD is less than the second EUD tolerance by the predetermined amount.

37. The arrangement of claim 36, wherein the intensity of the first portion of the further amount of energy is equal to the intensity of the first portion of the particular amount of energy when the first EUD is within the predetermined range of the first EUD tolerance, and wherein the intensity of the second portion of the further amount of energy is equal to the intensity of the second portion of the particular amount of energy when the second EUD is within the predetermined range of the second EUD tolerance.

38. The arrangement of claim 31, wherein the computer system is further adapted to transmit data associated with a resultant amount of energy to be applied to the target area when:
    at least one of the first EUD and the third EUD is within a predetermined range of the first EUD tolerance, and
    at least one of the second EUD and the fourth EUD is within the predetermined range of the second EUD tolerance.

39. The arrangement of claim 38, wherein the computer system is further adapted to simulate an application of a certain amount of energy upon the target area when each of the first EUD and the third EUD is outside the predetermined range of the first EUD tolerance, and wherein the certain amount of energy is determined using the POCS procedure.

40. The arrangement of claim 38, wherein the computer system is further adapted to simulate an application of a certain amount of energy upon the target area when each of the second EUD and the fourth EUD is outside the predetermined range of the first EUD tolerance, and wherein the certain amount of energy is determined using the POCS procedure.

41. The arrangement of claim 38, wherein the third EUD is less than the first EUD when the first EUD is greater than the first EUD tolerance by a predetermined amount, wherein the predetermined range is between about 0.01 Gy and about 1 Gy, and wherein the predetermined amount is greater than the predetermined range.

42. The arrangement of claim 38, wherein the computer system transmits the data to a distribution assembly.

43. The arrangement of claim 42, wherein the distribution assembly is adapted to transmit the resultant amount of energy to the target area.

44. The arrangement of claim 43, wherein the energy comprises radiation.

45. The arrangement of claim 44, wherein the radiation comprises at least one first radiation beam and at least one second radiation beam, wherein an intensity of the at least one first radiation beam is associated with at least one of the first EUD and the third EUD, and wherein an intensity of the at least one second radiation beam is associated with at least one of the second EUD and the fourth EUD.

46. The arrangement of claim 45, wherein the at least one first radiation beam comprises a first plurality of radiation beams, and wherein the at least one second radiation beam comprises a second plurality of radiation beams.

47. The arrangement of claim 29, wherein the first structure is a first organ and the second structure is a second organ.

48. The arrangement of claim 47, wherein the first organ is one of a first serial-type organ and a first parallel-type organ, and wherein the second organ is one of a second serial-type organ and a second parallel-type organ.

49. A method of treating a subject, comprising the steps of:
    simulating an application of a particular amount of energy upon a target area within a subject, wherein a first structure within the subject receives a first portion of the particular amount of energy, and a second structure within the subject receives a second portion of the particular amount of energy;
    determining whether a first equivalent uniform dose ("EUD") associated with the first portion of the particular amount of energy is greater than a first dose tolerance associated with the first structure; and
    determining whether a second EUD associated with the second portion of the particular amount of energy is greater than a second dose tolerance associated with the second structure.

50. The method of claim 49, wherein the first dose tolerance is a first EUD tolerance associated with the first structure, wherein the second dose tolerance is a second EUD tolerance associated with the second structure, and wherein the first EUD tolerance is different than the second EUD tolerance.

51. The method of claim 50, further comprising the steps of:
    simulating an application of a further amount of energy upon the target area, wherein the first structure receives a first portion of the further amount of energy, and the second structure receives a second portion of the further amount of energy;
    determining whether a third EUD associated with the first portion of the further amount of energy is greater than the first EUD tolerance; and
    determining whether a fourth EUD associated with the second portion of the further amount of energy is greater than the second EUD tolerance.

52. The method of claim 51, wherein the third EUD is less than the first EUD when the first EUD is greater than the first EUD tolerance by a predetermined amount, and wherein the fourth EUD is less than the second EUD when the second EUD is greater than the second EUD tolerance by the predetermined amount.

53. The method of claim 52, wherein the third EUD is greater than the first EUD when the first EUD is less than the first EUD tolerance by the predetermined amount, and wherein the fourth EUD is greater than the second EUD when the second EUD is less than the second EUD tolerance by the predetermined amount.

54. The method of claim 53, wherein the third EUD is equal to the first EUD when the first EUD is within a predetermined range of the first EUD tolerance, and wherein the fourth EUD is equal to the second EUD when the second EUD is within the predetermined range of the second EUD tolerance.

55. The method of claim 54, wherein an intensity of the first portion of the further amount of energy is less than an intensity of the first portion of the particular amount of energy when the first EUD is greater than the first EUD tolerance by the predetermined amount, and wherein an intensity of the second portion of the further amount of energy is less than an intensity of the second portion of the particular amount of energy when the second EUD is greater than the second EUD tolerance by the predetermined amount.

56. The method of claim 55, wherein the intensity of the first portion of the further amount of energy is greater than the intensity of the first portion of the particular amount of energy when the first EUD is less than the first EUD tolerance by the predetermined amount, and wherein the intensity of the second portion of the further amount of energy is greater than the intensity of the second portion of the particular amount of energy when the second EUD is less than the second EUD tolerance by the predetermined amount.

57. The method of claim 56, wherein the intensity of the first portion of the further amount of energy is equal to the intensity of the first portion of the particular amount of energy when the first EUD is within the predetermined range of the first EUD tolerance, and wherein the intensity of the second portion of the further amount of energy is equal to the intensity of the second portion of the particular amount of energy when the second EUD is within the predetermined range of the second EUD tolerance.

58. The method of claim 51, further comprising the step of determining the further amount of energy, wherein a projection onto convex sets ("POCS") procedure is used to determine the further amount of energy.

59. The method of claim 51, further comprising the step of transmitting data associated with a resultant amount of energy for an application to the target area when:
at least one of the first EUD and the third EUD is within a predetermined range of the first EUD tolerance, and
at least one of the second EUD and the fourth EUD is within the predetermined range of the second EUD tolerance.

60. The method of claim 59, further comprising the step of simulating an application of a certain amount of energy upon the target area when each of the first EUD and the third EUD is outside the predetermined range of the first EUD tolerance.

61. The method of claim 59, further comprising the step of simulating an application of a certain amount of energy upon the target area when each of the second EUD and the fourth EUD is outside the predetermined range of the first EUD tolerance.

62. The method of claim 59, wherein the predetermined range is between about 0.01 Gy and about 1 Gy, and wherein the particular amount is greater than the predetermined range.

63. The method of claim 59, further comprising the step of determining the further amount of energy, wherein a POCS procedure is used to determine the further amount of energy.

64. The method of claim 63, further comprising the step of determining the certain amount of energy, wherein the POCS procedure is used to determine the certain amount of energy.

65. The method of claim 59, wherein the data is transmitted to a distribution assembly.

66. The method of claim 65, further comprising the step of transmitting the resultant amount of energy to the target area.

67. The method of claim 66, wherein the energy comprises radiation.

68. The method of claim 67, wherein the radiation comprises at least one first radiation beam and at least one second radiation beam, wherein an intensity of the at least one first radiation beam is associated with at least one of the first EUD and the third EUD, and an intensity of the at least one second radiation beam is associated with at least one of the second EUD and the fourth EUD.

69. The method of claim 68, wherein the at least one first radiation beam comprises a first plurality of radiation beams, and wherein the at least one second radiation beam comprises a second plurality of radiation beams.

70. The method of claim 49, wherein the first structure is a first organ and the second structure is a second organ.

71. The method of claim 70, wherein the first organ is one of a first serial-type organ and a first parallel-type organ, and wherein the second organ is one of a second serial-type organ and a second parallel-type organ.

72. A method of treating a subject, comprising the steps of:
simulating an application of a particular amount of energy upon a target area within a subject, wherein a first structure within the subject receives a first portion of the particular amount of energy, and a second structure within the subject receives a second portion of the particular amount of energy; and
transmitting data associated with a resultant amount of energy to be applied to the target area when:
a first equivalent uniform dose ("EUD") associated with the first portion of the particular amount of energy is within a predetermined range of a first dose tolerance associated with the first structure, and
a second EUD associated with the second portion of the particular amount of energy is within the predetermined range of a second dose tolerance associated with the second structure.

73. The method of claim 72, wherein the first dose tolerance is a first EUD tolerance associated with the first structure.

74. The method of claim 73, wherein the second dose tolerance is a second EUD tolerance associated with the second structure.

75. The method of claim 74, wherein the first EUD tolerance is different than the second EUD tolerance.

76. A method of treating a subject, comprising the steps of:
simulating an application of a particular amount of energy upon a target area within a subject, wherein a first structure within the subject receives a first portion of the particular amount of energy;
determining whether a first equivalent uniform dose ("EUD") associated with the first portion of the particular amount of energy is greater than a first dose tolerance associated with the first structure; and
determining a further amount of energy to be simulated upon the target area using a projection onto convex sets ("POCS") procedure.

77. The method of claim 76, wherein a second structure with the subject receives a second portion of the particular amount of energy, and wherein the method further comprises the step of determining whether a second EUD associated with the second portion of the particular amount of energy is greater than a second dose tolerance associated with the second structure.

78. The method of claim 77, wherein the first dose tolerance is a first EUD tolerance associated with the first structure, wherein the second dose tolerance is a second EUD tolerance associated with the second structure, and wherein the first EUD tolerance is different than the second EUD tolerance.

79. The method of claim 78, further comprising the steps of:
  simulating an application of the further amount of energy upon the target area, wherein the first structure receives a first portion of the further amount of energy, and wherein the second structure receives a second portion of the further amount of energy;
  determining whether a third EUD associated with the first portion of the further amount of energy is greater than the first EUD tolerance; and
  determining whether a fourth EUD associated with the second portion of the further amount of energy is greater than the second EUD tolerance.

80. The method of claim 79, wherein the third EUD is less than the first EUD when the first EUD is greater than the first EUD tolerance by a predetermined amount, and wherein the fourth EUD is less than the second EUD when the second EUD is greater than the second EUD tolerance by the predetermined amount.

81. The method of claim 80, wherein the third EUD is greater than the first EUD when the first EUD is less than the first EUD tolerance by the predetermined amount, and wherein the fourth EUD is greater than the second EUD when the second EUD is less than the second EUD tolerance by the predetermined amount.

82. The method of claim 81, wherein the third EUD is equal to the first EUD when the first EUD is within a predetermined range of the first EUD tolerance, and wherein the fourth EUD is equal to the second EUD when the second EUD is within the predetermined range of the second EUD tolerance.

83. The method of claim 82, wherein an intensity of the first portion of the further amount of energy is less than an intensity of the first portion of the particular amount of energy when the first EUD is greater than the first EUD tolerance by the predetermined amount, and wherein an intensity of the second portion of the further amount of energy is less than an intensity of the second portion of the particular amount of energy when the second EUD is greater than the second EUD tolerance by the predetermined amount.

84. The method of claim 83, wherein the intensity of the first portion of the further amount of energy is greater than the intensity of the first portion of the particular amount of energy when the first EUD is less than the first EUD tolerance by the predetermined amount, and wherein the intensity of the second portion of the further amount of energy is greater than the intensity of the second portion of the particular amount of energy when the second EUD is less than the second EUD tolerance by the predetermined amount.

85. The method of claim 84, wherein the intensity of the first portion of the further amount of energy is equal to the intensity of the first portion of the particular amount of energy when the first EUD is within the predetermined range of the first EUD tolerance, and wherein the intensity of the second portion of the further amount of energy is equal to the intensity of the second portion of the particular amount of energy when the second EUD is within the predetermined range of the second EUD tolerance.

86. The method of claim 79, further comprising the step of transmitting data associated with a resultant amount of energy to be applied to the target area when:
  at least one of the first EUD and the third EUD is within a predetermined range of the first EUD tolerance, and
  at least one of the second EUD and the fourth EUD is within the predetermined range of the second EUD tolerance.

87. The method of claim 86, further comprising the steps of:
  determining a certain amount of energy to be simulated upon the target area using the POCS procedure when each of the first EUD and the third EUD is outside the predetermined range of the first EUD tolerance; and
  simulating an application of the another amount of energy upon the target area.

88. The method of claim 86, further comprising the steps of:
  determining another amount of energy to be simulated upon the target area using the POCS procedure when each of the second EUD and the fourth EUD is outside the predetermined range of the second EUD tolerance; and
  simulating an application of the another amount of energy upon the target area.

89. The method of claim 86, wherein the third EUD is less than the first EUD when the first EUD is greater than the first EUD tolerance by a predetermined amount, wherein the predetermined range is between about 0.01 Gy and about 1 Gy, and wherein the predetermined amount is greater than the predetermined range.

90. The method of claim 86, wherein the data is transmitted to a distribution assembly.

91. The method of claim 90, further comprising the step of transmitting the resultant amount of energy to the target area.

92. The method of claim 91, wherein the energy comprises radiation.

93. The method of claim 92, wherein the radiation comprises at least one first radiation beam and at least one second radiation beam, wherein an intensity of the at least one first radiation beam is associated with at least one of the first EUD and the third EUD, and wherein an intensity of the at least one second radiation beam is associated with at least one of the second EUD and the fourth EUD.

94. The method of claim 93, wherein the at least one first radiation beam comprises a first plurality of radiation beams, and wherein the at least one second radiation beam comprises a second plurality of radiation beams.

95. The method of claim 76, wherein the first structure is a first organ and the second structure is a second organ.

96. The method of claim 95, wherein the first organ is one of a first serial-type organ and a first parallel-type organ, and wherein the second organ is one of a second serial-type organ and a second parallel-type organ.

* * * * *